United States Patent [19]

Nakayama et al.

[11] 4,054,954
[45] Oct. 25, 1977

[54] METHOD OF PROVIDING HAIR AT THE SCALP

[75] Inventors: Taisuke Nakayama; Sokichi Nakajima, both of Tokyo, Japan

[73] Assignee: Tokyo Gihatsu Seikei Company Limited, Tokyo, Japan

[21] Appl. No.: 689,490

[22] Filed: May 24, 1976

[51] Int. Cl.² ........................ A61F 1/00; A61B 17/00
[52] U.S. Cl. ............................................. 3/1; 128/330
[58] Field of Search ................................. 3/1; 128/330

[56] References Cited

U.S. PATENT DOCUMENTS

| 3,553,737 | 1/1971 | Bauman | 3/1 |
| 3,621,837 | 11/1971 | Gindes | 3/1 |
| 3,755,824 | 9/1973 | Sperling | 3/1 |
| 3,842,439 | 10/1974 | Connelly et al. | 3/1 |
| 3,858,245 | 1/1975 | Naté | 3/1 |
| 3,914,801 | 10/1975 | Dick et al. | 3/1 |

Primary Examiner—Channing L. Pace
Attorney, Agent, or Firm—Phillips, Moore, Weissenberger, Lempio & Majestic

[57] ABSTRACT

The provision of hair at selected areas of the human scalp by attaching one or more hairpieces in strip form to a plurality of rings which pass through the scalp at spaced locations in such area and are threaded on an endless suture embedded under the scalp is disclosed. Surgical procedure for embedding the endless suture under the scalp and threading the rings thereon are described. A preferred combination of suture, rings and hairpiece is disclosed.

9 Claims, 8 Drawing Figures

U.S. Patent  Oct. 25, 1977  Sheet 1 of 2  4,054,954
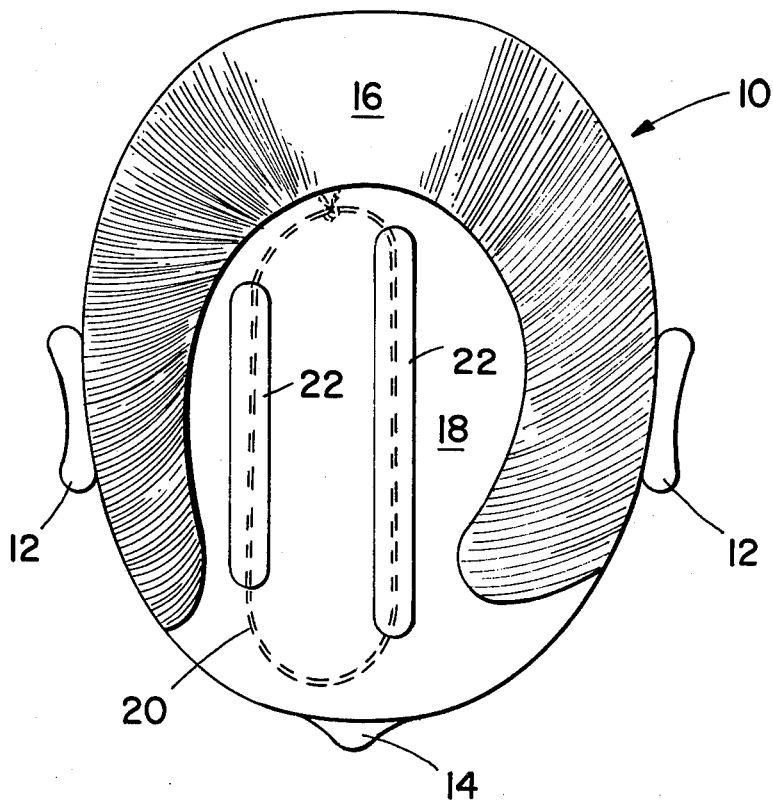
FIG _ 1
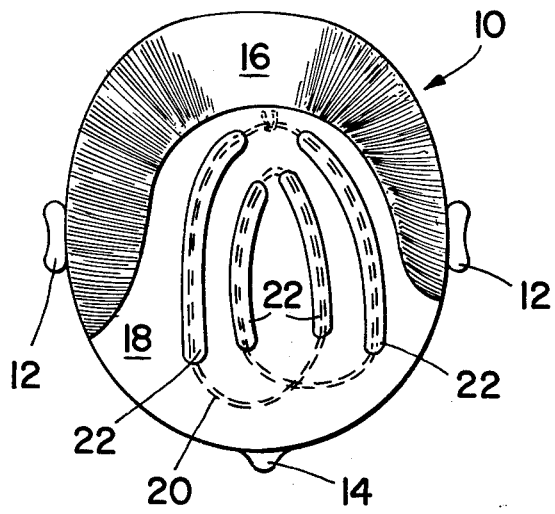
FIG _ 2
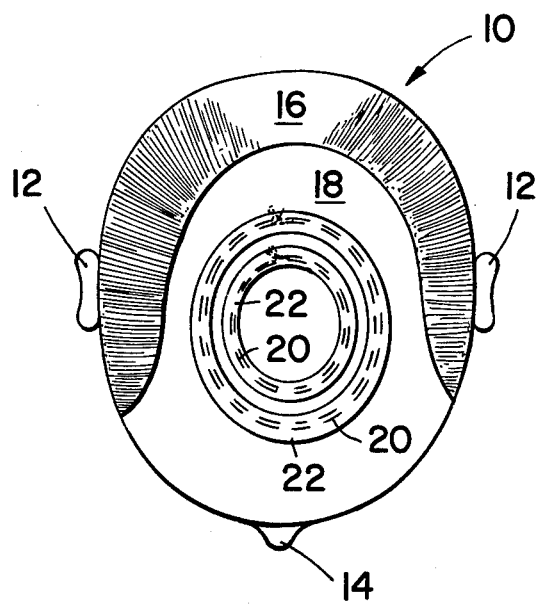
FIG _ 3

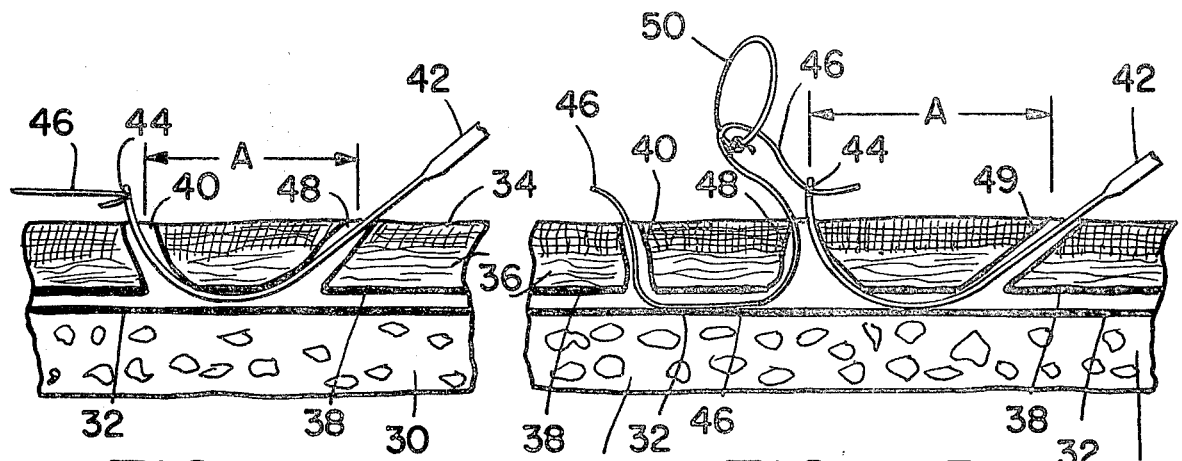
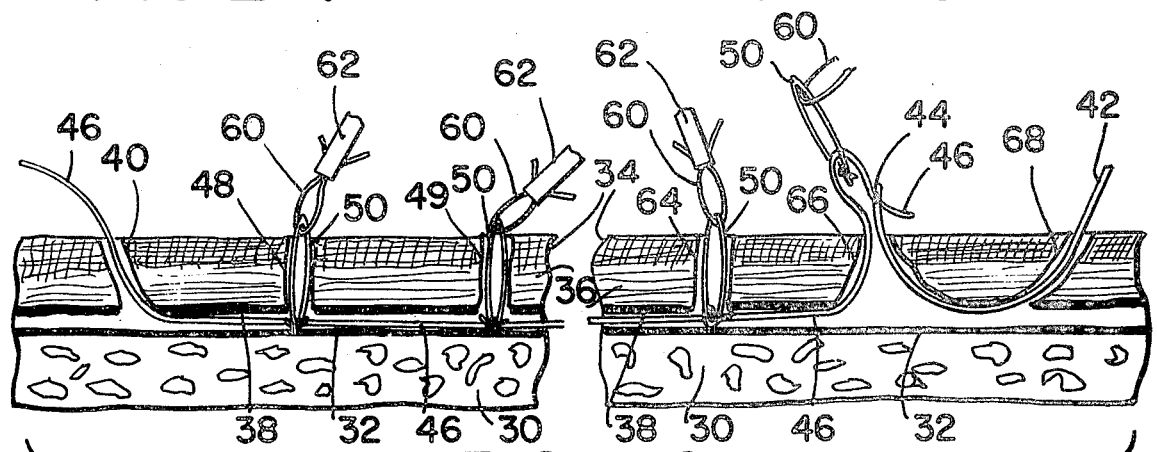
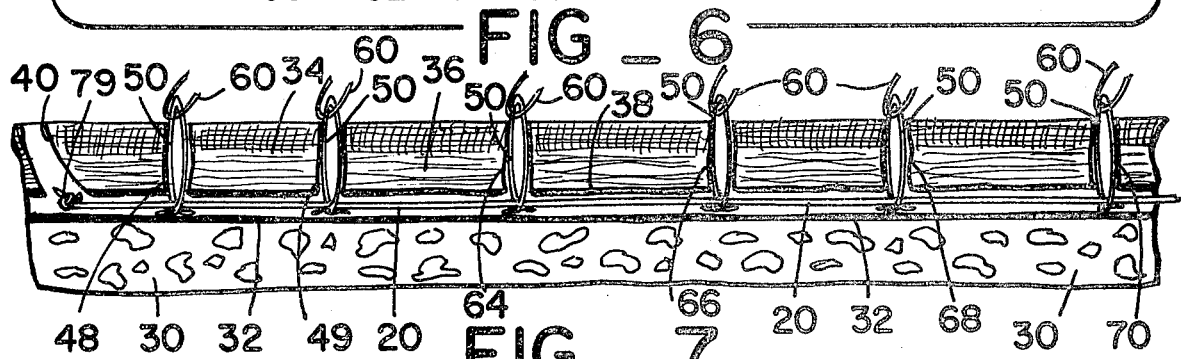
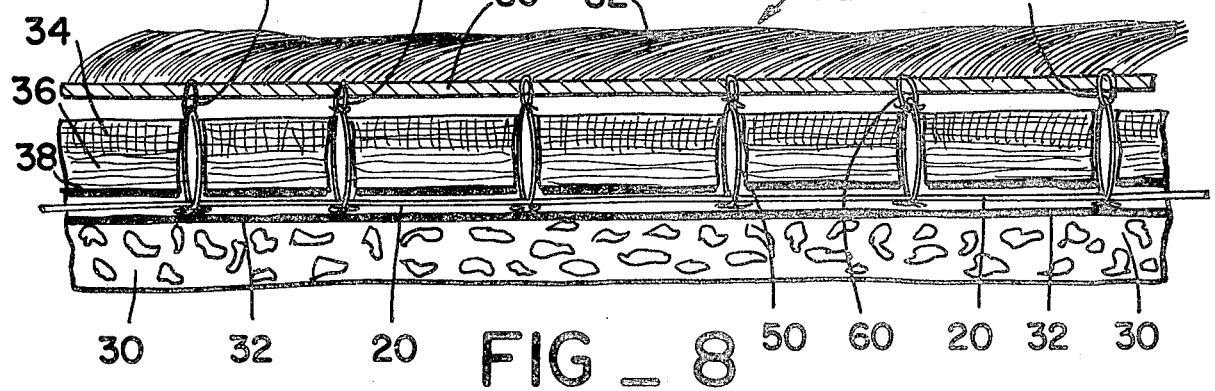

METHOD OF PROVIDING HAIR AT THE SCALP

BACKGROUND OF THE INVENTION

This invention relates to the concealment of baldness of the human scalp and more particularly to an improved method of and means for providing hair at the human scalp.

The use of hairpieces and wigs to cover bald spots of the human scalp is well known in the prior art. Various methods have been proposed for fastening the hairpieces in the desired position with respect to the scalp in order to avoid the accidental displacement thereof and consequent embarrassment.

For example, hairpieces have been made in the form of a skull cap designed to fit the head closely and have been attached to the scalp by various forms of adhesive. Such hairpieces are essentially temporary in their placement and impose strict limitations on the activity of the wearer. For example, any activity resulting in substantial perspiration at the scalp or direct physical contact even of liquids or fluids with the head of the wearer may result in displacement of the hairpiece.

Thus, it has been common in the prior art to attach hairpieces to the scalp more permanently by "weaving" techniques in which the remaining natural hair of the wearer is used to anchor the hairpiece to the scalp. Such techniques can only be used where there is sufficient remaining natural hair available adjacent the bald spot and tend to be expensive because the hairpiece must be periodically readjusted and reattached as the natural hair of the wearer grows longer and loosens the initial placement of the hairpiece.

In order to avoid the maintenance expense of "weaving" techniques, or where there is insufficient remaining natural hair available to allow such techniques to be used, various devices such as loops or stitches have been surgically implanted directly into the scalp to which a hairpiece may be attached. However, such devices have concentrated tensile forces applied by or to the hairpiece at limited points of the scalp tending to produce a tearing of the scalp tissue and resulting in discomfort if not actual pain and injury.

It is a primary object of this invention to provide an improved method of and means for providing hair at the human scalp which is substantially permanent and which facilitates normal maintenance of the hair and scalp without requiring frequent adjustment or reattachment.

It is another primary object of this invention to provide hair at the human scalp by a surgical method and means with improved comfort and safety.

SUMMARY OF THE INVENTION

Briefly, according to this invention, hair is provided at the scalp by embedding an endless suture having a plurality of rings threaded thereon in the scalp. The suture lies wholly beneath the exterior surface of the scalp and the rings threaded thereon extend through the scalp to the exterior surface thereof. A hairpiece is attached to the rings at the exterior surface of the scalp.

BRIEF DESCRIPTION OF THE DRAWING

The foregoing and other objects and features of advantage of this invention will be more fully understood from the following detailed description when read in conjunction with the attached drawings wherein:

FIG. 1 is a top plan view of a human head with the location of a suture embedded under the scalp, according to the teaching of this invention, indicated by dotted lines and with two hairpieces shown schematically as attached to such suture.

FIG. 2 is a top plan view of a human head similar to FIG. 1 but showing a different arrangement of suture and hairpieces according to the teaching of this invention.

FIG. 3 is a top plan view of a human head similar to FIG. 1 but showing a still different arrangement of sutures and hairpieces according to the teaching of this invention.

FIG. 4 is a fragmentary cross-sectional view of a portion of the human scalp and scull showing the beginning of the surgical procedure for embedding an endless suture under the scalp in accordance with the teaching of this invention.

FIG. 5 is a fragmentary cross-sectional view similar to FIG. 4 of a larger portion of the human scalp and skull showing the threading of the first ring on the suture as it is embedded under the scalp.

FIG. 6 is an enlarged fragmentary cross-sectional view similar to FIGS. 4 and 5, of a still larger portion of the human scalp and skull showing intermediate steps in the surgical procedure for embedding a suture under the scalp in accordance with the teaching of this invention.

FIG. 7 is a fragmentary cross-sectional view of the human scalp and skull upon completion of the surgical procedure for embedding a suture under the scalp in accordance with the teaching of this invention.

FIG. 8 is a fragmentary cross-sectional view of the human scalp and skull similar to FIG. 7 but showing a hairpiece connected to the rings threaded on the suture embedded under the scalp in accordance with the teaching of this invention.

DESCRIPTION OF PREFERRED EMBODIMENTS

Referring to FIG. 1, a stylized top plan view of a human head 10 is shown with the ears 12 and nose 14 also shown in stylized form for purposes of orientation. Similarly, a stylized representation of an area 16 of the scalp of the head 10 which has natural hair growing therein is shown, the remaining area 18 of the scalp being represented as bald.

According to a basic feature of this invention, an endless suture 20 forming a closed figure of the desired shape is embedded under the scalp in the bald area 18. As shown in FIG. 1, the closed figure formed by the endless suture 20 is a simple oval shape defining a surface underlying the scalp and generally parallel to the exterior surface of the skull. As will be more fully described hereinafter, a plurality of connecting rings (not shown in FIG. 1) are threaded on the endless suture 20 and pass through the scalp to the exterior thereof at spaced locations along the endless suture 20.

One or more hairpieces 22 are attached to the connecting rings by means of thread of appropriate strength, for example, in order to hold the hairpieces 22 in place on the bald area 18 of the scalp of the head 10. According to the preferred embodiment of this invention, the hairpieces 22 comprise an elongated strip of film made of transparent, translucent or opaque synthetic resin, resilient rubber or synthetic rubber having a thickness less than about 0.04 inch (1 mm.). A plurality of hairs are attached to the film and project therefrom in the manner of natural hair to cover and conceal the bald area 18.

According to this invention, the closed figure formed by the endless suture 20 may have any desired shape as required in view of the shape of the bald area 18 of the scalp. It is preferred that the figure be smoothly curved in order to reduce the concentration of stresses therein at sharp corners, however, complex figures may be formed by the endless suture as shown in FIG. 2, and more than one endless suture may be embedded under the scalp, as shown in FIG. 3, where the bald areas to be concealed are large.

Referring to FIG. 2, a slightly smaller stylized representation of a human head 10 is shown wherein the same reference numerals as used in FIG. 1 are used to identify corresponding parts and wherein the bald area 18 is somewhat larger. Thus, as shown in FIG. 2, the endless suture 20 may have a greater length and form a complex closed figure including a looped portion, for example, in order to provide for the attachment of a larger number of hairpieces 22 of appropriate length and in appropriate position to insure concealment of the bald area 18 of the scalp.

Similarly, as shown in FIG. 3, more than one endless suture 20 may be embedded under the scalp in order to enable attachment of an appropriate number of hairpieces and their appropriate positioning to insure concealment of the bald area of the scalp. As shown in FIG. 3, which is a stylized representation of the top of a human head 10 similar to FIGS. 1 and 2 and in which the reference numerals of FIGS. 1 and 2 are used to designate corresponding parts, the closed figures formed by two or more sutures may have a symmetric relationship to each other although it would also be possible for the figures to overlap each other or to be spaced from each other within bald area 18 of the scalp. As also shown in FIG. 3, it is possible for the hairpieces 22 to be coextensive with the endless sutures 20 if necessary or desirable in order to provide for the concealment of the bald area 18.

Referring to FIGS. 4 through 8, the surgical procedure for embedding the suture 20 under the scalp and threading the connecting rings thereon in accordance with the teaching of this invention is shown. The various physical dimensions shown in FIGS. 4 through 8 have been exaggerated in order to facilitate the understanding of the surgical procedure and the positional relationship of the embedded suture to the scalp and skull as well as the positional relationship of the connecting rings to the suture with respect to the scalp and skull.

Referring to FIG. 4, an enlarged fragmentary cross-section of the skull 30 is shown. The heavy line identified by the reference numeral 32 represents the periosteum or fibrovascular membrane that covers and nourishes the exterior surface of the skull 30. The scalp is shown in cross-section overlying the skull 30 and comprises the epidermis or skin shown as a single layer 34 overlying the occipitofrontal muscle represented by the layer 36. The heavy line designated by the reference numeral 38 represents the galea which is the epicranial aponeurosis which connects the bellies of the occipitofrontal muscle.

After suitably anesthetizing the scalp as by injecting an appropriate local anesthetic, such as Novocaine, for example, in the scalp, together with an appropriate blood coagulant at the affected area, the surgical procedure for embedding the suture 20, according to the teaching of this invention is begun, as shown in FIG. 4, by first making an incision through the various layers 34, 36 of the scalp including the galea 38 but avoiding the periosteum to the extent possible. A needle 42 is then inserted through the layers 34, 36 of the scalp, including the galea 38 and again avoiding the periosteum to the extent possible. The needle 42 is inserted at a point spaced from the incision by a distance represented by the double-headed arrow A which is preferably one-half inch to 2 inches (1 cm to 5 cm). As shown in FIG. 4, the needle 42 may be curved in order to facilitate the passing of the needle under the scalp between the galea 38 and periosteum and out of the incision 40. The free end of the needle 42 which projects from the incision 40 is provided with an eye 44 and one end of an appropriate filament or thread 46 which is to be formed into the endless suture 20 is passed through the eye 44 in the conventional manner. The needle 42 is then withdrawn from the scalp drawing the filament 46 into the incision 40, under the scalp between the galea and periosteum, and out of the scalp through the opening 48 in the scalp produced by the original insertion of the needle 42 therein. The free end of the filament 46 is now removed from the eye 44 of the needle 42 and pulled to provide an appropriate free length of filament 46 at the opening 48.

Referring to FIG. 5, the needle 42 is then reinserted through the layers 34 and 36 of the scalp and between the galea 38 and periosteum 32 exiting the scalp through the opening 48 previously formed by the needle 42. Thus, a further opening 49 is formed through the scalp at a distance A from the first opening 48.

A connecting ring 50 is threaded on the filament 46 and the free end of the filament again passed through the eye 44 of the needle in the conventional manner. Upon withdrawal of the needle 42 from the scalp, the filament 46 will again be carried under the scalp between the galea 38 and periosteum 32 exiting from the scalp through the new opening 49 and tending to pull the connecting ring 50 into the opening 48.

As best shown in FIG. 6, an appropriate thread 60 is passed through the connecting ring 50 and the free ends of the thread 60 are securely held by an appropriate surgical clamp 62 to prevent the connecting ring 50 from becoming too deeply embedded in the scalp for subsequent utilization. FIG. 6 also shows that the above described steps of the surgical procedure are repeated to provide a plurality of additional spaced openings 64, 66 and 68 through the scalp in addition to the opening 49 and to position connection rings 50 threaded on the suture 46 in each of the openings 49, 64, 66 and 68.

Although the cross-sectional views of FIG. 4 through 8 are necessarily shown in the plane of the paper on which they are drawn making it appear that the connecting rings 50 lie in a straight line, it is pointed out that such cross-sectional views are actually taken along a length of the periphery of the closed figure which will result when the filament 46 is formed into a closed suture 20 embedded under the scalp, as shown in FIGS. 1-3. Thus, referring to FIG. 7, the above-described steps of the surgical procedure according to this invention are repeated with the needle being inserted through the scalp at points spaced along the desired closed figure and with the final insertion of the needle being through the incision 40 so that the ends of the filament 46 may be tied together in a knot as indicated at 79 to form the endless suture 20 under the scalp, in accordance with the teaching of this invention.

Prior to tying the free ends of the filament into the knot 79, the filament is slightly tensioned to insure proper seating of the rings 50. The bond between the galea and the periosteum will absorb a portion of such tensioning with the balance of the tensioning being absorbed by the connecting rings 50. The threads 60 and surgical clamps 62 prevent the connecting rings 50 from being drawn too far into the scalp by such tensioning and after the knot 79 is tied, the surgical clamps 62 are removed leaving the threads 60 available for further use.

It will be noted that the connecting rings 50 are also formed of a filament having its free ends knotted together to form the ring. As shown in FIGS. 6 through 8, the knot of the rings 50 is preferably located between the galea and and periosteum when the surgical procedure is completed. Thus, the knot in the rings 50 will help to anchor them in the scalp.

According to the preferred embodiment of this invention, monofilament nylon is preferred both for the filament of which the endless suture 20 is made and the filament of which the connecting rings 50 are made. Such nylon monofilament preferably has a diameter of about 1.5 mm. Each connecting ring 50 is preferably made of a piece of such nylon monofilament having a length of about ¼ inch (0.50 cm) and thus the connecting rings 50 are flexible enough to collapse within the openings 48, 49 64, 66, 68 and 70 rather than standing open as suggested in the drawing.

Referring to FIG. 8, the threads 60 are used to attach to the connecting rings 50 a hairpiece 22 having a film base 80 with hair 82 projecting from the upper surface thereof as described hereinabove. In the preferred embodiment, the threads 60 which may be made of silk having an appropriate color are sewn through the film base 80 of the hairpiece 22 anf firmly knotted.

From the above detailed description and the drawing it will be understood that forces applied to the hairpiece 22 will be distributed to one or more of the connecting rings 50. The connecting rings 50 will be urged to move axially within the openings in which they are received with a minimum of peeling or tearing action. The endless suture 20 will further distribute the forces involved and will tend to act as a shock absorber where localized forces are applied to a small number of connecting rings 50. Thus, the use of a plurality of independent hairpieces 22 is facilitated and the total stress applied to the connecting rings 50 and endless suture 20 is absorbed and distributed.

It has been found that this invention results in greater comfort for the wearer and reduced possibility of injury or pain when tensile forces are applied to the hairpieces 22. The cleaning of the scalp under the hairpieces is also facilitated and more effective concealment of bald areas of the scalp is provided. It is believed that those skilled in the art will make obvious changes in the preferred embodiment of this invention as shown in the drawing and described hereinabove. For example, other materials may be used for the endless suture 20 and connecting rings as well as different hairpieces 22 and different means for attaching the hairpiece to the connecting rings without departing from the teaching of this invention.

What is claimed is:

1. In the method of providing hair at the scalp wherein a preformed hairpiece is attached to an anchoring suture in the scalp, the improvement comprising the steps of:

a. inserting a needle having an eye at the free end thereof in said scalp at a first point;
   b. passing said needle under the exterior surface of said scalp and out of said scalp at a reference point spaced from said first point;
   c. threading a suture filament through said eye at said free end of said needle and withdrawing said needle from said scalp drawing said suture filament into said scalp at said reference point, under the exterior surface of said scalp and out of said scalp at said first point;
   d. reinserting said needle in said scalp at a second point spaced from said first point;
   e. passing said needle under the exterior surface of said scalp and out of said scalp at said first point;
   f. threading a first ring on said suture filament at said first point and then threading said suture filament through said eye at said free end of said needle at said first point;
   g. again withdrawng said needle from said scalp drawing said suture filament into said scalp at said first point, under the exterior surface of said scalp and out of said scalp at said second point, whereby said first ring is pulled into said scalp at said first point, and
   h. attaching a hairpiece to said first ring at the exterior surface of said scalp.

2. In the method of providing hair at the scalp as claimed in claim 1 the additional steps of serially reinserting said needle in said scalp at further points each spaced from a preceding point, passing said needle under the exterior surface of said scalp and out of said scalp at said preceding point, threading a further ring on said suture filament and said suture filament through said eye of said needle at each preceding point, and withdrawing said needle from said scalp drawing said suture filament into said scalp at said preceding point, under the exterior surface of said scalp and out of said scalp at said further point.

3. In the method of providing hair at the scalp as claimed in claim 2 the additional steps of selecting said points of insertion of said needle to form said suture filament into a closed figure with the final point of insertion of said needle being through said reference point and the steps of tensioning and tying said suture filament at said reference point into an endless embedded suture.

4. In the method of providing hair at the scalp as claimed in claim 3 the additional steps of passing each of a plurality of threads through a different one of said rings and clamping each of said plurality of threads at the exterior surface of said scalp when the associated one of said rings is threaded on said suture.

5. In the method of providing hair at the scalp as claimed in claim 4 the additional step of unclamping each of said plurality of threads after said suture filament is tied at said reference point and employing said plurality of threads to attach said hairpiece to said rings.

6. In the method of providing hair at the scalp as claimed in claim 5 the additional step of passing said needle through the epidermis, occipitofrontal muscle and galea of said scalp avoiding the periosteum to the extent possible.

7. In the method of providing hair at the scalp as claimed in claim 6 the initial step of injecting local anesthetic to anesthetise the entire scalp for a period of time sufficient to perform the remaining steps of said method.

8. In the method of providing hair at the scalp as claimed in claim 5 the additional step of embedding a second endless suture in said scalp with a second plurality of rings thereon and threads in said rings by repeating the steps claimed in claim 5 with respect to said second suture, second plurality of rings and second plurality of threads.

9. In the method of providing hair at the scalp wherein a preformed hairpiece is attached to an anchoring suture in the scalp the improvement comprising the steps of:
 a. inserting a needle having an eye at the free end thereof into said scalp at a first point;
 b. passing said needle under the exterior surface of said scalp and out of said scalp at a reference point spaced from said first point;
 c. threading a suture filament through said eye at said free end of said needle and withdrawing said needle from said scalp drawing said suture filament into said scalp at said reference point, under the exterior surface of said scalp and out of said scalp at said first point;
 d. reinserting said needle into said scalp at a second point spaced from said first point;
 e. passing said needle under the exterior surface of said scalp and out of said scalp at said first point;
 f. threading a first ring on said suture filament at said first point and threading said suture filament through said eye at said free end of said needle at said first point;
 g. again withdrawing said needle from said scalp drawing said suture filament into said scalp at said first point, under the exterior surface of said scalp and out of said scalp at said second point, whereby said first ring is pulled into said scalp at said first point;
 h. serially reinserting said needle into said scalp at further points each spaced from a preceding point, passing said needle under the exterior surface of said scalp and out of said scalp at said preceding point, threading a further ring on said suture filament and said suture filament through the eye of said needle at each preceding point, and withdrawing said needle from said scalp drawing said suture filament into said scalp at said preceding point, under the exterior surface of said scalp and out of said scalp at said further point; selective said reference point, said first point and said further points to form a closed figure with the final point of insertion of said needle being through said reference point whereby both ends of said suture filament extend out of said scalp at said reference point;
 i. tensioning and tying said suture filament at said reference point into an endless embedded suture; and
 j. attaching a hairpiece to said first ring and each said further ring at the exterior surface of said scalp.

* * * * *

UNITED STATES PATENT OFFICE
CERTIFICATE OF CORRECTION

Patent No. 4,054,954          Dated   October 25, 1977

Inventor(s)  Taisuke Nakayama and Sokichi Nakajima

It is certified that error appears in the above-identified patent and that said Letters Patent are hereby corrected as shown below:

Column 4, line 50 - delete "connection" and substitute --connecting-- therefor.

Column 8, line 19 - delete "selective" and substitute --selecting-- therefor.

Signed and Sealed this

Third Day of April 1979

[SEAL]

Attest:

RUTH C. MASON
Attesting Officer

DONALD W. BANNER
Commissioner of Patents and Trademarks